United States Patent [19]
Herkes

[11] Patent Number: 5,149,809
[45] Date of Patent: Sep. 22, 1992

[54] SYNTHESIS OF 2-ALKYLHEXAHYDROPYRIMIDINES FROM NITRILES

[75] Inventor: Frank E. Herkes, Wilmington, Del.

[73] Assignee: E. I. Du Pont de Nemours and Company, Wilmington, Del.

[21] Appl. No.: 798,605

[22] Filed: Nov. 26, 1991

[51] Int. Cl.$^5$ .................. C07D 239/04; C07B 43/04
[52] U.S. Cl. ...................................... 544/242
[58] Field of Search ........................... 544/242

[56] References Cited

U.S. PATENT DOCUMENTS 4,404,379  9/1983  Hayek .................................. 544/335

*Primary Examiner*—Mark L. Berch
*Attorney, Agent, or Firm*—Earl L. Handley

[57] ABSTRACT

Process for producing 2-alkylhexahydropyrimidines from 1,3-diamines and alkyl nitriles using a hydrogenation catalyst.

7 Claims, No Drawings

SYNTHESIS OF 2-ALKYLHEXAHYDROPYRIMIDINES FROM NITRILES

FIELD OF THE INVENTION

This invention relates to a process for the preparation of 2-alkylhexahydropyrimidines and N-alkyl homologs, i.e., compounds having the formula:

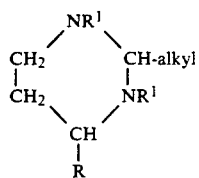

where the alkyl group has 1 to 18 carbon atoms, R is hydrogen or an alkyl group of 1 to 15 carbon atoms, and $R^1$ is hydrogen or an alkyl group of 1 to 18 carbon atoms, and at least one $R^1$ is hydrogen.

BACKGROUND OF THE INVENTION

Hexahydropyrimidines are produced by condensation of aldehydes or ketones with 1,3-diamines (U.S. Pat. No. 4,404,379 to Hajek et al.; Reibsomer, J. L., & Morey, G. H., J. Org. Chem., 1950, 15, 245; Evans, R. F., Aust. J. Chem., 1967, 1967, 20, 1634–61). Water is a by-product in these reactions and must be removed either to favor the imine equilibrium or for product purification. Generally, the condensation is acid or lewis acid catalyzed and run in solvents (DE Patent No. 1,670,093 to BASF). In some cases the open-chain tautomer is produced as a co-product which further contaminates the desired hexahydropyrimidines.

A process has been found to make alkyl-, dialkyl-, and trialkylhexahydropyrimidines in high yield without the formation of water or its open-chain tautomer. The invention is selective to the hexahydropyrimidines with only ammonia as the by-product. Cyclization, ammonia elimination and hydrogenation occur rapidly to produce the hexahydropyrimidine derivative in a single reaction step.

The hexahydropyrimidines have use as catalysts in the production of polyurethanes and epoxies (U.S. Pat. No. 3,787,416), as fungicides (U.S. Pat. No. 3,872,120), emulsifiers (U.S. Pat. No. 4,579,593 to Stanley), pharmaceuticals (J. Pharm. Sci., 1968, 57, 1817–19 and EP 226,511), fuel oil additives (U.S. Pat. No. 3,936,279), antioxidants (U.S. Pat. No. 3,787,416), and light stabilizers for olefins (U.S. Pat. No. 4,404,302 to Gupta et al).

SUMMARY OF THE INVENTION

This invention is a process for the preparation of hexahydropyrimidines which comprises reacting an alkyl nitrile having 1 to 18 carbon atoms with a 1,3-diaminoalkane having 3 to 18 carbon atoms or an N-alkyl-1,3-diaminoalkane in which the alkane has 3 to 18 carbon atoms, and in which the N-alkyl group has 1 to 18 carbon atoms, in the presence of a hydrogenation catalyst at a temperature in the range of 70 to 150 degrees C. and hydrogen at a pressure of 100 to 1000 psig, said alkyl nitrile being present in a 1 to 3 molar ratio to the amount of the 1,3-diaminoalkane or the N-alkyl-1,3-diaminoalkane. Suitable hydrogenation catalysts include supported cobalt, supported nickel, supported ruthenium, supported iron, supported rhodium, supported palladium, Raney cobalt and Raney nickel. If the catalyst is a supported catalyst, suitable supports include: alumina, silica, kieselguhr, carbonate, and cordierite.

The reaction may be carried out in a solvent for the nitrile. Suitable solvents include alcohols and ethers.

The alkyl nitrile may be a mononitrile or a dinitrile; for example, adiponitrile is satisfactory.

DETAILED DESCRIPTION

The reaction to produce hexahydropyrimidines from alkyl nitriles and 1,3-diamines under hydrogenation conditions include any substituted 1,3-diamines or N-alkyl-1,3-diamines. Propane and pentane diamine are preferred diamines, but diamines of C3 to C18 are satisfactory. Both the N-alkyl group and the alkyl nitrile can have alkyl substitution of C1 to C18.

The temperature employed in the reaction is preferably about 90° C. Hydrogenation of nitriles documented in the art range from 70° to 150° C., preferably 90° to 125° C. Because the activation energy for the reductive alkylation of the intermediate imine is approximately 31 Kcal/mole, higher temperatures will tend to favor hexahydropyrimidine formation. However, the activation energy for nitrile hydrogenation is in the range of 12 Kcal/mole (e.g., favored at lower temperatures) and thus a temperature compromise must be met to optimize both reactions. The above 90° to 150° C. temperature range fulfills this requirement.

Low concentrations of hydrogenation catalyst produce a desirable slow hydrogenation of nitrile. Nitrile hydrogenation solvents such as alcohols (e.g., methanol, ethanol or isopropanol) or ethers (e.g., tetrahydrofuran or dioxane) can also be used. Generally, catalysts and reaction conditions that favor secondary amine formation are desirable.

Nitrile hydrogenation catalysts such as supported cobalt, nickel, ruthenium, iron, rhodium, palladium, and Raney ® catalysts (e.g., cobalt and nickel) can be used in this process. Catalyst supports for these metals include alumina, silica, kieselguhr and basic supports such as carbonates and cordierite.

EXAMPLES

Example 1: 2,4-Diethylhexahydropyrimidine

Into a 300 ml stainless steel batch stirred autoclave was charged 70 g (96.7% purity, 0.66 mole) 1,3-diaminopentane, 80 g propionitrile (1.45 moles) and 3 g of wet Raney ® nickel (W. R. Grace Raney ® 2800) powder. The reactor was purged twice at 25° C. with hydrogen followed by pressurization with 50 psig hydrogen. The mixture was stirred at 500 rpm while heating to 90° C. At 90° C., the reactor was repressured to 650 psi with hydrogen, and stirring at 1200 rpm commenced. A 500 ml stainless steel ballast cylinder was inserted in series with the hydrogen feed to allow measurement of hydrogen uptake by propionitrile at constant reactor pressure. The pressure in the ballast was set at 800–850 psig and repressured when the gauge dropped to approximately 650 psig.

After 4 hours of heating and stirring, the mixture was cooled to room temperature and a sample taken through a high pressure sample valve on the reactor. The reactor pressure was then reduced to 1 atmosphere. Gas chromatographic (GC) capillary analysis of the product mixture indicated a 58% conversion of the 1,3-diaminopentane and 80.8% yield of the 2,4-diethylhexahydropyrimidine. The mixture was then allowed to stand 16 hours at 25° C. and 50 psig hydrogen pressure. Reanalysis of the mixture showed conversion of the 1,3-diaminopentane had increased to 72% and the yield of hexahydropyrimidine to 96.4%. An additional 25 ml propionitrile was added to a reactor inlet port by means of a glass syringe at atmospheric pressure. The reactor was repurged with hydrogen and brought to the original reaction conditions and allowed to run for 3 more hours. Analysis of the final product mixture showed a 92% conversion of 1,3-diaminopentane and 92.8% yield of 2,4-diethylhexahydropyrimidine.

After replacing the reactor atmosphere with nitrogen, the cooled product was filtered away from the catalyst under a nitrogen atmosphere. Fractional distillation under reduced pressure on a 36 inch Teflon ® spinning band column yielded 27 g of clear liquid product with >99% purity having a b.p. of 84° C. at 22 mm Hg.

Example 2: 2-Methyl-4-Ethylhexahydropyrimidine

Sixty grams of 1,3-diaminopentane (96.7% purity, 0.569 mole), 60 g acetonitrile (1.46 moles) and 1 g of wet Raney ® nickel (Raney 2800) catalyst were charged to a 300 ml stainless steel autoclave reactor. The mixture was stirred and heated at 90° C. and 500 psig hydrogen pressure for 6 hours. Capillary GC analysis of the cooled product indicated a 36% conversion of 1,3-diaminopentane and 97.4% yield of 2-methyl-4-ethyl-hexahydropyrimidine. The reactor was recharged with 25 ml (19.5 g) additional acetonitrile and run at 90° C. and 500 psig for 21 hours. Capillary GC analysis of the mixture indicated a 92.1% conversion of 1,3-diaminopentane and 98% yield of 2-methyl-4-ethylhexahydropyrimidine, b.p. 71° C./20 mm Hg. The structure was confirmed by comparison with a mass spectrum of the hexahydropyrimidine obtained by the condensation of 1,3-diaminopentane and acetaldehyde at 50° C.

Example 3: 2-Isobutyl-4-Ethylhexahydropyrimidine

Forty grams of 1,3-diaminopentane (96.8% purity, 0.45 mol), 76 g (1.1 moles) isobutyronitrile and 2 g wet Raney ® nickel (Raney 2800) catalyst were charged to the 300 ml autoclave described in Example 1. The mixture was stirred and heated at 90° C. and 500 psig hydrogen for 6 hours. The product was cooled and allowed to stand 16 hours at 25° C. and 50 psig hydrogen pressure. The mixture was then heated at 100° C. and 500 psig hydrogen for an additional 15 hours. Analysis of the final product mixture by capillary GC analysis showed a 64% conversion of 1,3-diaminopentane, 87.6% conversion of isobutyronitrile and 97% yield to 2-isobutyl, 4-ethylhexahydropyrimidine.

The filtered product was fractionally distilled under vacuum on a 36 inch Teflon ® spinning band column to yield 31.7 g of >98% pure 2-isobutyl, 4-ethylhexahydropyrimidine having a b.p. of 53° C./1 mm Hg.

Example 4: 2-Methylhexahydropyrimidine

Thirty-five grams (0.47 mole) 1,3-diaminopropane, 60 g acetonitrile (1.46 moles) and 2 g of wet Raney ®) nickel (Raney 2800) catalyst was charged to a 300 ml batch reactor described in Example 1. The mixture was stirred and heated at 90° C. and 500 psig hydrogen pressure for 7 hours. The product mixture was cooled and sampled. Analysis of the filtered product by capillary GC analysis indicated a 98.5% conversion of 1,3-diaminopropane and 94% yield of 2-methylhexahydropyrimidine.

The product was filtered from the catalyst under nitrogen and fractionally distilled under vacuum on a 36 inch Teflon ® spinning band column yielding 20.4 g of 99% purity 2-methylhexahydropyrimidine having a b.p. of 82° C./88 mm Hg.

Example 5: 2-Methyl-4-Ethylhexahydropyrimidine using Nickel Catalyst

Ninety grams (96.8% purity, 0.854 mole) 1,3-diaminopentane, 60 g acetonitrile (1.46 moles) and 3 g powdered nickel on alumina catalyst were charged to a 300 ml autoclave described in Example 1. The mixture was stirred and heated at 90° C. and 650 psig pressure for 6 hours followed by cooling to 25° C. Analysis of the filtered product on a capillary GC column showed a 42.9% conversion of 1,3-diaminopentane and 94% yield of 2-methyl-4-ethylhexahydropyrimidine.

Example 6: 2-Methyl-4-Ethylhexahydropyrimidine using Raney ® Co

Ninety grams (96.8% purity, 0.854 mole) 1,3-diaminopentane, 60 g acetonitrile (1.46 moles) and 3 g Cr promoted Raney ® cobalt catalyst were charged to a 300 ml autoclave described in Example 1. The mixture was stirred and heated at 90° C. and 650 psig pressure for 5 hours followed by cooling to 25° C. Analysis of the filtered product on a capillary GC column showed a 14% conversion of 1,3-diaminopentane and 96.2% yield of 2-methyl-4-ethylhexahydropyrimidine Example 7: 2-Methyl-4-Ethylhexahydropyrimidine Ninety grams (96.8% purity, 0.854 mole) 1,3-diaminopentane, 60 g acetonitrile (1.46 moles) and 3 g wet Raney ® nickel catalyst were charged to a 300 ml autoclave described in Example 1. The mixture was stirred and heated at 90° C. and 650 psig pressure for 6 hours followed by cooling to 25° C. Analysis of the filtered product on a capillary GC column showed a 85% conversion of 1,3-diaminopentane and 98% yield of 2-methyl-3-ethylhexahydropyrimidine.

Example 8: 2,3-Dimethyl-4-Ethylhexahydropyrimidine

Thirty-five grams of 3-(N-methylamino)aminopentane (99% purity, 0.302 mole), 60 g acetonitrile (1.46 moles) and 2 g of Raney ® nickel catalyst were charged to a 300 ml stainless steel autoclave reactor. The mixture was stirred and heated at 90° C. and 500 psig hydrogen pressure for 7 hours. Capillary GC analysis of the cooled product indicated a 96.5% conversion of 3-(N-methylamino)aminopentane and 82.8% yield of 2,3-dimethyl-4-ethylhexahydropyrimidine. Fifty-five grams were recovered and vacuum distilled on a 36 inch Teflon ® spinning band column to yield 18.1 g (68% recovery) of 2,3-dimethyl-4-hexahydropyrimidine (97.6% purity) having a bp of 81° C. at 20 mm Hg.

Example 9

Fifty grams of 1,3-diaminopentane (99%, 0.485 mole), 116 g (1.07 moles) adiponitrile and 2.3 g Raney ® nickel were charged to a 300 cc autoclave reactor. The mixture was stirred and heated at 90° C. and 650 psig hydrogen pressure for 10 hours. The mixture was cooled and filtered under nitrogen. Capillary GC analysis of the filtered product indicated a 56% conversion of 1,3-diaminopentane and 59% yield of 2-(4-cyanobutyl)-4-ethylhexahydropyrimidine.

I claim:

1. A process for the preparation of hexahydropyrimidines which comprises reacting an alkyl nitrile having 1 to 18 carbon atoms with a 1,3-diaminoalkane having 3 to 18 carbon atoms or an N-alkyl-1,3-diaminoalkane in which the alkane has 3 to 18 carbon atoms, and in which the N-alkyl group has 1 to 18 carbon atoms, in the presence of a hydrogenation catalyst at a temperature in the range of 70 to 150 degrees C. and hydrogen at a pressure of 100 to 1000 psig, said alkyl nitrile being present in a 1 to 3 molar ratio to the amount of the 1,3-diaminoalkane or the N-alkyl-1,3-diaminoalkane.

2. The process of claim 1 in which the hydrogenation catalyst is selected from the group consisting of supported cobalt, supported nickel, supported ruthenium, supported iron, supported rhodium, supported palladium, Raney cobalt and Raney nickel.

3. The process of claim 1 in which the amine is 1,3-diaminopentane.

4. The process of claim 2 in which the catalyst is a supported catalyst, and the support is selected from the group consisting of alumina, silica, kieselguhr, carbonate, and cordierite.

5. The process of claim 4 in which the process is carried out in a solvent for the nitrile.

6. The process of claim 5 in which the solvent is selected from the group consisting of alcohols and ethers.

7. The process of claim 1 in which the alkyl nitrile is an alkyl dinitrile.

* * * * *